(12) United States Patent
Ponce

(10) Patent No.: US 7,608,419 B2
(45) Date of Patent: Oct. 27, 2009

(54) METHOD AND APPARATUS FOR DETECTING AND QUANTIFYING BACTERIAL SPORES ON A SURFACE

(75) Inventor: Adrian Ponce, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 334 days.

(21) Appl. No.: 10/987,202

(22) Filed: Nov. 12, 2004

(65) Prior Publication Data

US 2005/0136508 A1 Jun. 23, 2005

Related U.S. Application Data

(60) Provisional application No. 60/624,068, filed on Nov. 1, 2004, provisional application No. 60/519,851, filed on Nov. 13, 2003.

(51) Int. Cl.
| | |
|---|---|
| C12Q 1/06 | (2006.01) |
| C12Q 1/04 | (2006.01) |
| C12Q 1/00 | (2006.01) |
| C12M 1/34 | (2006.01) |

(52) U.S. Cl. .............. 435/39; 435/34; 435/31; 435/4; 435/287.1

(58) Field of Classification Search .......... 435/29–39, 435/4, 287.1
See application file for complete search history.

(56) References Cited

U.S. PATENT DOCUMENTS

| | | | |
|---|---|---|---|
| 4,560,665 A | 12/1985 | Nakae et al. ............... 436/172 |
| 4,943,522 A | 7/1990 | Eisinger et al. ............ 435/7.25 |
| 4,965,211 A | 10/1990 | Wieder et al. ............... 436/543 |
| 5,124,268 A | 6/1992 | Dakubu ..................... 436/537 |
| 5,792,330 A | 8/1998 | Petersen et al. ............. 204/452 |
| 5,830,769 A | 11/1998 | Wieder et al. ............... 436/536 |
| 5,875,960 A | 3/1999 | Rosen ........................ 435/39 |
| 5,876,960 A | 3/1999 | Rosen ........................ 435/39 |
| 6,136,549 A | 10/2000 | Feistel ....................... 435/7.1 |
| 6,242,268 B1 | 6/2001 | Wieder ...................... 436/536 |
| 6,569,630 B1 | 5/2003 | Vivekananda et al. ......... 435/6 |

(Continued)

FOREIGN PATENT DOCUMENTS

EP 03707656 2/2007

(Continued)

OTHER PUBLICATIONS

Seveus et al., Time-resolved fluorescence imaging of europeum chelate label in immunohistochemistry and in situ hybridization, 1992, Cytometry, 13, 329-338.*

(Continued)

*Primary Examiner*—Ruth A Davis
*Assistant Examiner*—Sheridan R Macauley
(74) *Attorney, Agent, or Firm*—Steinfl & Bruno

(57) ABSTRACT

A method and an apparatus for detecting and quantifying bacterial spores on a surface. In accordance with the method: a matrix including lanthanide ions is provided on the surface containing the bacterial spores; functionalized aromatic molecules are released from the bacterial spores on the surface; a complex of the lanthanide ion and the aromatic molecule is formed on the surface; the complex of the lanthanide ion and the aromatic molecule is excited to generate a characteristic luminescence of the complex on the surface; and the bacterial spores exhibiting the luminescence of the complex on the surface are detected and quantified.

31 Claims, 6 Drawing Sheets

U.S. PATENT DOCUMENTS

Figure 1A:
Figure 1B:
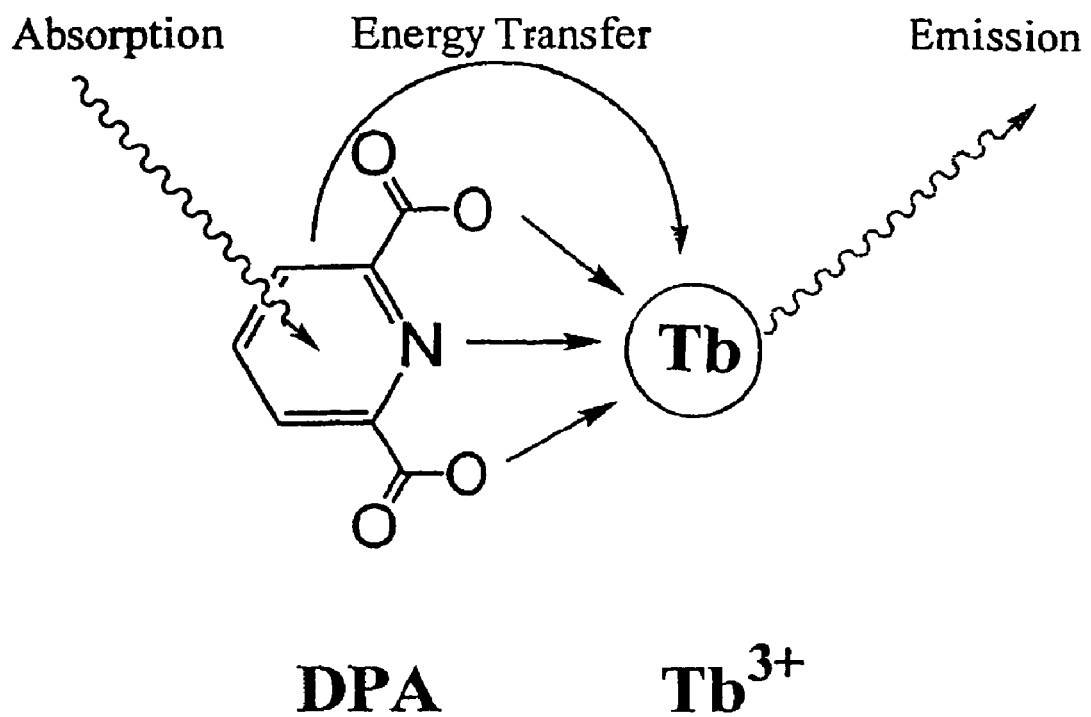
Figure 1C:
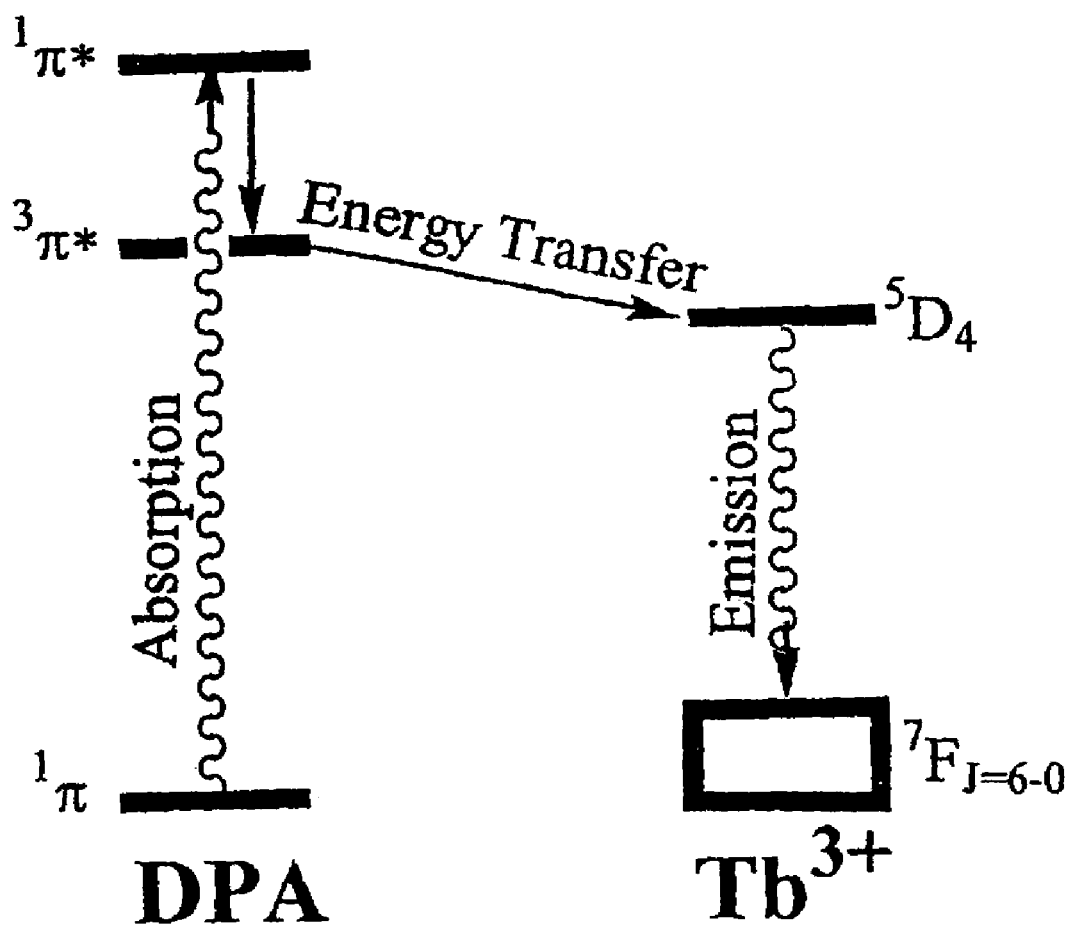

| | | | |
|---|---|---|---|
| 6,599,715 B1 | 7/2003 | Vanderberg et al. | 435/34 |
| 6,766,817 B2 | 7/2004 | da Silva | |
| 6,918,404 B2 | 7/2005 | Dias da Silva | |
| 7,066,586 B2 | 6/2006 | da Silva | |
| 7,306,930 B2 | 12/2007 | Ponce | 435/34 |
| 2002/0135772 A1* | 9/2002 | Bornhop et al. | 356/450 |
| 2003/0064427 A1 | 4/2003 | Felkner et al. | 435/31 |
| 2003/0138876 A1 | 7/2003 | Ponce et al. | 435/34 |
| 2004/0014154 A1 | 1/2004 | Ponce et al. | 435/7.32 |
| 2005/0136508 A1 | 6/2005 | Ponce | |
| 2006/0292664 A1 | 12/2006 | Ponce | |
| 2007/0031916 A1 | 2/2007 | Ponce | 435/34 |
| 2007/0117175 A1 | 5/2007 | Ponce | 435/29 |
| 2008/0113384 A1 | 5/2008 | Ponce | 435/34 |

FOREIGN PATENT DOCUMENTS

| | | |
|---|---|---|
| WO | 00/63422 | 10/2000 |
| WO | 01/83561 A2 | 11/2001 |
| WO | 03/024491 A2 | 3/2003 |
| WO | 03/067211 A3 | 8/2003 |
| WO | 03065009 A2 | 8/2003 |
| WO | WO 03/065009 A2 * | 8/2003 |

OTHER PUBLICATIONS

Belgrader et al., A minisonicator to rapidly disrupt bacterial spores for DNA analysis, 1999, Analytical Chemistry, 71, 4232-4236.*

Beeby, A., et al. , . "Luminescence imaging microscopy and lifetime mapping using kinetically stable lanthanide (III) complexes", *Journal of Photochemistry and Photobiology*, B: Biology 57, pp. 83-89 (2000).

Branda, S., et al., "Fruiting body formation by *Bacillus subtilis,*" *PNAS*, vol. 98, No. 20, 11621-11626 (Sep. 25, 2001).

Horrocks Jr., W., et al., "Lanthanide Ion Luminescense Probes of the Structure of Biological Macromolecules", *American Chemical Society*, No. 14, pp. 384-392 (1981).

Koehler, T.M., "*Bacillus anthracis* Genetics and Virulence Gene Regulation," *Current Topics in Microbiology & Immunology*, vol. 271, pp. 143-164, 2002.

Lester, E., et al., "An Anthrax "Smoke" Detector", *IEEE Engineering in Medicine and Biology*, pp. 38-42 (Sep./Oct. 2002).

Lutterbach, M.T.S., et al., "Biofilm Formation on Brass Coupons Exposed to Cooling Water", *Brazilian Journal of Chemical Engineering*, vol. 14, No. 1 (Mar. 1997).

Lutterbach, M.T.S., et al., "Biofilm Formation Monitoring in an Industrial Open Water Cooling System," *Revista de Microbiologia*, 28, pp. 106-109 (1997).

Mitchell, A.C., et al., "Measurement of nanosecond time-resolved fluorescence with a directly gated interline CCD camera", Journal of Microscopy, vol. 206, Pt. 3, pp. 233-238 (Jun. 2002).

Murrell, W. G., *Chemical Composition of Spores and Spore Structures* Chapter 7, 1969.

Nicholson, W.L., et al., "Resistance of Bacillus Endospores to Extreme Terrestrial and Extraterrestrial Environments", *Microbiology and Molecular Reviews*, vol. 64, No. 3, pp. 548-572 (Sep. 2000).

Pastuska, J., et al., "Bacterial and fungal aerosol in indoor environment in Upper Silesia, Poland," *Atmospheric Environment*, 34, pp. 3833-3842 (2000).

Pierson, D., et al., "Microbial Contamination of Spacecraft", *Gravitational and Space Biology Bulletin* 14 (2) (Jun. 2001).

Rode, et al., "Induced Release of Dipicolinic Acid From Spores of Bacillus Megaterium", *Journal of Bacteriology*, vol. 79, pp. 650-656 (1960).

Rose, L., et al., "Swab Materials and *Bacillus anthracis* Spore Recovery from Nonporous Surfaces", *Emerging Infectious Diseases*, vol. 10, No. 6, www.cdc.gov/eid (Jun. 2004).

Sacks, L.E., "Chemical Germination of Native and Cation-Exchanged Bacterial Spores with Trifluoperazine," *Applied and Environmental Biology*, vol. 56, No. 4, pp. 1185-1187 (1990).

Selvin, P.R., "The Renaissance of Flourescense Resonance Energy Transfer", *Natural Structural Biology*, vol. 7, No. 9, pp. 730-734 (2000).

Uchida, I., et al., "Cloning and Characterization of a Gene Whose Product Is a trans-Activator of Anthrax Toxin Synthesis", *Journal of Bacteriology*, vol. 175, No. 17 (Sep. 1993).

Vaid, A., et al., "The destruction by microwave radiation of bacterial endospores and amplification of the released DNA", *Journal of Applied Microbiology*, vol. 85, pp. 115-122 (1998).

Vereb, G., et al., "Temporarily and Spectrally Resolved Imaging Microscopy of Lanthanide Chelates", Biophysical Journal, vol. 74, pp. 2210-2222 (May 1998).

Xiao, M., et al., "An improved instrument for measuring time-resolved lanthanide emission and resonance energy transfer", *Review of Scientific Instruments*, vol. 70, No. 10 (Oct. 1999).

Beverly, M.B., et al., "Analysis of Dipicolinic Acid in Bacterial Spores by Electron Monochromator-Mass Spectrometry," *Presented at the 47th ASMS Conference on Mass Spectrometry and Allied Topics*, Dallas, Texas, 2 pages total (Jun. 13-17, 1999).

Gómez-Hens, A., et al., "Terbium-Sensitized Luminescence: A Selective and Versatile Analytical Approach," *Trends in Analytical Chemistry*, vol. 21, No. 2, pp. 131-141 (2002).

Hindle, A., et al., "Dipicolinic Acid (DPA) Assay Revisited and Appraised for Spore Detection," *Analyst*, vol. 124, pp. 1599-1604 (1999).

Paratamian, S.A., "Anthrax Detection, The Faster, The Better," *Microbiology* 12, Internet:<http://www.college.ucla.edu/webproject/micro12/honorprojects/Partamianp01/MicroHonorsWebPage.html> pp. 1-8 (Spring 2001).

Rosen, D.L., "Bacterial Endospore Detection Using Photoluminescence From Terbium Dipicolinate," *Reviews Analytical Chemistry*, vol. 18, No. 1-2, pp. 1-21 (1999).

Abstract of Scholl, P., et al., "Immunoaffinity Based Phosphorescent Sensor Platform for the Detection of Bacterial Spores," *Proceedings of the SPIE*, vol. 3913, 1 page total (2002).

Sorasaenee, K., et al., "Cooperative Binding of Tb(III) Supramolecular Complexes with Dipicolinic Acid: Improved Sensitivity of Metal-Contaning Lumophores in Biomedical Applications," *Division of Chemistry and Chemical Engineering, California Institute of Technology*, Pasadena, California, 1 page total (2003).

Warth, A.D., "Liquid Chromatographic Determination of Dipicolinic Acid from Bacterial Spores," *Applied and Environmental Microbiology*, vol. 38, No. 6, pp. 1029-1033 (Dec. 1979).

Elbanowski, et al., "The Lanthanides Probes In Investigation Of Biochemical Systems", Journal of Photochemistry and Photobiology A: Chemistry, vol. 99, pp. 85-92 (1996).

Lamture, et al., Intensity Luminescent Immunoreactive Conjugates of proteins and Dipicolinate-Based Polumeric Tb (III) Chelates, Biconjugate Chemistry, vol. 6, pp. 88-92 (1995).

Pellegrino, P., et al., "Enhanced spore detection using dipicolinate extaction techniques", Analytica Chimicha Acta, vol. 455, No. 2, pp. 1667-177 (Jan. 8, 2002).

Pellegrino, P.M., et al., "Bacterial endospore detection using terbium dipicolinate photoluminescence in the presence of chemical and biological materials", Analytical Chemistry 1998 U.S. Army Res. Lab, vol. 70, No. 9, pp. 1755 (1998).

Pierson, D., et al., "Microbial Contamination of Spacecraft", *Gravitational and Space Biology Bulletin* 14 (2) (Jun. 2001).

Scholl, P., et al., "Immunoaffinity based phosphorescent sensor platform for the detection of bacterial spores", Proc. SPIE Int Soc Opt Eng, vaol. 3913, pp. 204-214 (2000).

PCT International Search Report for PCT/US03/03036 filed on Jan. 31, 2003 in the name of California Institute of Technology.

PCT International Search Report for PCT/US2006/022988 filed on Jun. 13, 2006 in the name of California Institute of Technology.

PCT Written Opinion for PCT/US2006/022988 filed on Jun. 13, 2006 in the name of California Institute of Technology, et al.

A. J. Alvarez, M. Khanna, G a. Toranzos, and G Stotzky, "Amplification of DNA bound on clay minerals," *Molecular Ecology*, vol. 7, pp. 775-778, 1998.

R. I. Amann, W. Ludwig, and K. H. Schleifer, "Phylogenetic Identification and in-Situ Detection of Individual Microbial-Cells without Cultivation," *Microbiological Reviews*, vol. 59, pp. 143-169, 1995.

P. Belgrader. W. Benett, D. Hadley. I. Richards, P. Stratlon, R. Mariella and F. P. Milanovich, "Infectious disease-PCR detection of bacteria in seven minutes." *Science*, vol. 284. pp. 449-450, 1999.

P. Belgrader, C.I. Elkin. S.B, Brown. S.N. Nasarabadi, R.G. Langlois, F.P. Milanovich, B.W. Colston, and G.D. Marshall. "A reusable flow-through polymerase chain reaction instrument for the continuous monitoring of infectious biological agents," *Analyt Chem*. vol. 75, pp. 3446-3450, 2003.

M. Carl. R. Hawkins, N. Coulson. I. Lowe. D.L. Robertson. W.M. Nelson, R.W. Titball and J.N. Woody. "Detection of spores of Bacillus•anthracis using the polymerase chain-reaction," *J. Infectious Diseases*, vol. 165, pp. 1145-1148. 1992.

A. Castro and R.T. Okinaka, "Ultrasensitive, direct detection of a specific DNA sequence of *Bacillus anthracis* in solution," *Analyst* vol. 125. pp. 9-11, 1999.

B D. Church and H. Halvorson, "Dependence of the Heat Resistance of Bacterial Endospores on Their Dipicolinic acid Content," *Nature*, vol. 183, pp. 124-125, 1959.

R. Connally, D. Veal, and J. Piper, "High resolution detection of fluorescently labeled microorganisms in environmental samples using time-resolved fluorescence microscopy," *Ferns Microbiology Ecology*, vol. 41, pp. 239-245, 2002.

Enserink M: ANTHRAX: Biodefence Hampered by Inadequate Tests. *Science* 2001, 294:1266-1267.

J.W. Ezzell. T.G. Absbire. S.F. Little, B.C. Lidgerding. and C. Brown, "Identification of *Bacillus-anthracis* by using monoclonal-antibody to cell-wall antibody to cell-wall galacttose-N-acetylglucosamine polysaccharide," J. Clin. Mlcrobiol, vol. 28. pp. 223-231, 1990.

Grenthe I: Stability Relationships among the Rare Earth Dipicolinates. *Journal of the American Chemical Society* 1961, 83: 360-364.

W.D. Griffiths and G.A.L. Decosemo. "The assessment of bioaerosols-A critical- review," *J. Aerosol Sci* vol. 25, pp. 1425-1458. 1994.

W.D. Griffiths, I.W. Stewan. S.J. Futter, S.L. Upton, and D. Mark, "The development of sampling methods for the assessment of indoor bioaerosols," *J. Aerosol ScL*, vol. 28. pp. 437-457, 1997.

J. Ho, "Future of biological aerosol detection," *Analyrica Chimica Acta*, vol. 457, pp. 125-148, 2002.

P.M. Holland. R.D. Abramson, R. Watson. and D.H. Gelfand, "Detection of specific polymerase chain-reaction product by utilizing the 5'-3' exonuclease activity of thermus-aquaticus DNA-polymerase," in *Proc. Nat Acad. Sci. USA*, vol. 88. 1991. pp. 7276-7280.

G. Horneck, H. Bucker, and G. Reitz, "Long-Term Survival of Bacterial-Spores in-Space," *Life Sciences and Space Research*), vol. 14, pp. 41-45, 1994.

W. D. Horrocks Jr., "Lanthanide Ion Luminescence in Coordination Chemistry and Biochemistry," in *Progress in Inorganic Chemistry*, vol. 31. New York: Wiley, 1984, p. 1.

Hunnicutt, D. W., M. J. Kempf, and M. J. McBride. 2002. Mutations in *Flavobacteriumjohnsoniae gldF* and *gldG* disrupt gliding motility and interfere with membrane localization of GIdA. *J. Bacteriol.* 184: 2370-2378.

T.V. Inglesby, D.A. Henderson, J.G. Bartlett, M.S. Ascher. E. Eitzen, A.M. Friedlander, J. Hauer. J. McDade, M.T. OSterholm, T. O•Toole. G. Parker, T.M.mPerl, P.K. Russell, and K. Tonat, "Anthrax as a biological weapon-Medical and public health management," *JAMA*, vol. 281, pp. 1735-1745. 1999.

K. Ito, K. Nakagawa, S. Murakami, H. Arakawa, and M. Maeda, "Highly sensitive simultaneous Bioluminescent measurement of acetate kinase and pyruvate phosphate dikinase activities using a firefly luciferase-luciferin reaction and its application to a tandem Bioluminescent enzyme immunoassay," *Analytical Sciences*, vol. 19, pp. 105-109, 2003.

F.W. Janssen, A.J. Lund. and L.E. Anderson, "Colorimetric assay for dipicolinic acid in bacterial spores," *Science*, vol. 127. pp. 26-27, 1958.

M. Johns. L. Harrington, R.W. Titball, and D.L. Leslie. "Improved methods for the detection of *Bacillus-anthracls* spores by the polymerase chain-reaction," *Lett. AppL Microbiol* vol. 18, pp. 236-238. 1994.

Kempf. M. J. And M. J. McBride. 2000. Transposon insertions in the *Flavobacterium johnsoniae ftsX* gene disrupt gliding motility and cell division. *J. Bacteriol* 182:1671-1679.

J. Knight, "US postal service puts anthrax detectors to the test," *Nature*, vol. 417, pp. 579-579, 2002.

L. J. Kricka, "Chemiluminescence and bioluminescence," *Analytical Chemistry*, vol. 71, pp. 305R-308R, 1999.

D.B. Lacy and R.J. Collier. "Structure and function of anthrax toxin," in *Anthrax, Current Topics in Microbiology and Immunology*, vol. 271, pp. 61-85, 2002.

D. Lawrence, S. Heitefuss, and H.S.H. Seifert, "Differentiation of Bacillusanthracis from bacillus-cereus by gas-chromatographic whole-cell fatty-acid analysis," *J. Clin. Microbiol.* vol. 29, pp. 1S08-1512, 1991.

Lester E et al: "A second-generation anthrax smoke detector" IEEE Engineering in Medicine and Biology Magazine, IEEE Service Center, Pisacataway, NJ, US, vol. 23, No. 1, Jan. 2004 (Jan. 2004), pp. 130-135, XP001201545 ISSN: 0739-5175 the whole document.

A. Lundin, "Use of firefly luciferase in ATP-related assays of biomass, enzymes, and metabolites," Bioluminescence and Chemiluminescence, Pt C, vol. 305, pp. 346-370,2000.

R. L. Mancinelli and M. Klovstad, "Martian soil and UV radiation: microbial viability assessment on spacecraft surfaces," Planetary and Space Science, vol. 48, pp. 1093-1097, 2000.

G Manfredi, A. Spinazzola, N. Checcarelli, and A. Naini, "Assay of mitochondrial ATP synthesis in animal cells," Methods in Cell Biology. vol. 65, vol. 65, pp. 133-145, 2001.

A. C. Mitchell, J. E. Wall, J. G. Murray, and C.G. Morgan, "Direct modulation of the effective sensitivity of a CCD detector: a new approach to time-resolved fluorescence imaging," *Journal of Microscopy-Oxford*, vol. 206, pp. 225-232, 2002.

M. M. Moeseneder, J. M. Arrieta, G Muyzer, C. Winter, and G J. Herndl, "Optimization of terminal-restriction fragment length polymorphism analysis for complex marine bacterioplankton communities and comparison with denaturing gradient gel electrophoresis," *Applied and Environmental Microbiology*, vol. 65, pp. 3518-3525, 1999.

M. Paidhungat, B. Setlow, A. Driks, and P. Setlow, "Characterization of spores of *Bacillus subtilis* which lack dipicolinic acid," Journal ofBacteriology, vol. 182, pp. 5505-5512, 2000.

A.P. Phillips and K.L. Martin. "Evaluation of a microfluorometer in Immunofluorescence assays of individual spores of bacillus-anthracis and bacillus-cereus," *J.ImnwntJlogical MetiuJdJ*, vol. 49, pp. 271-282. 1982.

A.P. Phillips, K.L. Martin, N. L. Cross, and R.G. Drake, "Evaluation of immunoradiometric and Elisa versions of a microtitre plate assay for bacillusanlhracis spores," *J. Immunological Merhod1*, vol. 70, pp. 75-81, 1984.

A.P. Phillips and K.L. Martin. "Quantitative immunofluorescenoe studies of the serology of bacillus-anthracis spores," Appl. Environmenral Microbiol., vol. 46, pp. 1430-1432, 1983.

V. Ramisse, G. Patra. H. Garrigue. J.L. Guesdon, and M. Mock, "Identification and characterization of *Bacillus anthracis* by multiplex PCR analysis of sequences on plasmids pX01 and pX02 and chromosomal DNA," Ferns *Microbiol* Lett. vol. 145, pp. 9-16, 1996.

C. Redmond, M.J. Pearce, R.T. Manchee, and B.P. Berdal, "Deadly relic of the great war," *Nature.* vol. 393. pp. 747-748.1998.

Rosen DL, Sharpless C, McGown LB: Bacterial Spore Detection and Determination by Use of Terbium Dipicolinate Photoluminescence. *Anal Chem* 1997, 69: 1082-1085.

Rosen DL: Wavelength Pair Selection for Bacterial Endospore Detection by Use of Terbium Dipicolinate Photoluminescence. *Appl Optics* 1998, 37: 805-807.

M. Schena, D. Shalon, R. W. Davis, and P. O. Brown, "Quantitative Monitoring of Gene-Expression Patterns with a Complementary-DNA Microarray," *Science*, vol. 270, p. 467470, 1995.

P. Sneath, "Longevity of micro-organisms," *Nature*, vol. 195, pp. 643-646, 1962.

PJ. Stopa, "The flow cytometry of *Bacillus anthracis* spores revisited," *Cytometry*, vol. 41, pp. 237- 244, 2000.

B.N. Strizhkov, A.L. Drobyshev, V.M. MikhailovIch, and A.D. Mirzabekov, "PCR amplification on a microarray of gel-immobilized oligonucleotides: Detection of bacterial toxin- and drug-resistant genes and their mutations," *Biotechnique.*, vol. 29. pp. 844-851, 2000.

V. Torsvik, I. Goksoyr, and F. L. Daae, "High Diversity in DNA of Soil Bacteria," *Applied and Environmental Microbiology*, vol. 56, pp. 782-787, 1990.

M. Varughese, A.V. Teixeira, S.H. Liu. And S.H. Leppla. "Identification of a receptor.binding region within domain 4 of the protective antigen component of anthrax *toxin." Infection and Immunity*, vol. 67, pp. 1860-1865, 1999.

Venkateswaran, K., M. Kempf. F. Chen, M. Satomi, W. Nicholson, and R. Kern. 2003. *Bacillus nealsonii* sp. nov. isolated from a spacecraft assembly facility, whose spores are gamma-radiation resistant. *Int J. Syst. Evol. Microbiol* 53:165-172.

G Vereb, E. Jares-Erijman, P. R. Selvin, and T. M. Jovin, "Temporally and spectrally resolved imaging microscopy of lanthanide chelates," *Biophysical Journal*, vol. 74, pp. 2210-2222, 1998.

R. H. Vreeland, W. D. Rosenzweig, and D. W. Powers, "Isolation of a 250 million-year old halotolerant bacterium from a primary salt crystal," *Nature*, vol. 407, pp. 897-900, 2000.

D. L. Balkwill, F. R. Leach, J. T. Wilson, J. F. McNabb, and D. C. White, "Equivalence of Microbial Biomass Measures Based on Membrane Lipid and Cell-Wall Components, Adenosine-Triphosphate, and Direct Counts in Subsurface Aquifer Sediments," *Microbial Ecology*, vol. 16, pp. 73-84, 1988.

Balzani V, Decola L, Prodi L, Scandola F: Photochemistry of Supramolecular Species. *Pure App Chem* 1990, 62:1457-1466.

Balzani V: Supramolecular Photochemistry. *Pure App Chem* 1990, 62:1099-1102.

Belgrader, et al. "A minisonicator to rapidly disrupt bacterial spores for DNA analysis", Analytical Chemistry, 71, pp. 4232-4236 (1999).

Cable, Morgan L, et al, Bacterial Spore Detection by [Tb3+ (macrocycle)(dipicolinate)] luminescence, *Beckman Institute, California Institute of Technology, Pasadena, CA 91125, and in Situ Instruments Section, Jet Propulsion Laboratory, Pasadena, CA* 91109 (2007).

I. Henderson. C.J. Duggleby, and P.C.B. Turnbull. "Differentiation of Bacillus-Anthracis from other BacIllus-cereus group bacteria with the Pcr," *Int. J. Systematic Bacteriol.*, vol. 44. pp. 99-105. 1994.

J. G Jones, "Effect of Environmental-Factors on Estimated Viable and Total Populations of Planktonic Bacteria in Lakes and Experimental Enclosures," *Freshwater Biology*, vol. 7, pp. 67-91, 1977.

Lehn JM: Supramolecular Chemistry-Scope and Perspectives Molecules, Supermolecules, and Molecular Devices. *Angewandte Chemie-International Edition in English 1988*, 27:89-112.

N.A. Logan, J.A. Carman, I. Melling, and R.C.W. Berkeley. "Identification of *Bacillus-antbracis* by api tesIS," *J. Medical Microbial.* vol. 20. pp. 75-85, 1985.

McBride, M. J. And M. J. Kempf. 1996. Development of techniques for the genetic manipulation of the gliding bacterium *Cytophaga johnsonae*. J. Bacteriol. 178: 583-590.

McBride, et al, Autonomous Detection of Aerosolized *Bacillus anthracis* and *Yersiniapestis*, *Anal. Chemistry*, (2003) 75, 5293-5299.

C. G Morgan and A. C. Mitchell, "Fluorescence lifetime imaging: An emerging technique in fluorescence microscopy," *Chromosome Research*, vol. 4, pp. 261-263, 1996.

W. Nicholson and P. Setlow; "Sporulation, germination and outgrowth," *Molecular biology methods for bacillus*, S. Cutting, Ed. Sussex, England: John Wiley and Sons, 1990, 391-450).

G. Patra, P. Sylvestre, V. Ramisse, I. Therasse, and IL. Guesdon. "Isolation of a specific chromosomic DNA sequence of *Bacillus anthracis* and its possible use in diagnosis," *Fems Immunol. Medical Microblol.*, vol. 15. pp. 223--231.1996.

Sabbatini N, Guardigli M, Lehn J M: Luminescent Lanthanide Complexes as Photochemical Supramolecular Devices. *Coord Chem Rev 1993*, vol. 123:201-228.

Seveus, et al., "Time-resolved fluorescence imaging of europheu label in immnunohistochemistry and in situ hybridization"', Cytometry, 13. pp. 329-338 (1998).

Sinha S: *Systematics and the Properties of the Lanthanides*. Edited by Sinha S: NATO ASI Series 109; 1983.

Slieman et al, Role of dipocolinic acid in survival of bacillus subtilis spores exposed to artificial and solar UV radiation, *Applied and Environmental Microbiology*, Vol. 67, No. 3, 1274-1279, (2001).

P.C.B. Turnbull. "Definitive identification of *Bacillus anthsacis-*A review," *J. Applied Microbiol*, vol. 87. pp. 237-240. 1999.

D. C. White, W. M. Davis, J. S. Nickels, J. D. King, and R. J. Bobbie, "Determination of the Sedimentary Microbial Biomass by Extractable Lipid Phosphate," *Oecologia*, vol. 40, pp. 51-62, 1979.

USPTO Non-final Office Action, U.S. Appl. No. 11/404,382, Adrian Ponce, Mail Date Jul. 10, 2008.

USPTO Final Office Action, U.S. Appl. No. 11/404,382, Adrian Ponce, Mail Date Jan. 15, 2008.

USPTO Non-final Office Action, U.S. Appl. No. 11/404,382, Adrian Ponce, Mail Date Aug. 16, 2007.

A. Ponce, "Live/Dead Spore Assay Using DPA-Triggered Tb Luminescence," *NASA Tech Briefs*, vol. accepted, 27(#3), pp. 6a-7a, 2003.

A. Ponce. "Lateral-flow immunoassay with DPA-triggered Tb luminescenoe," *NASA tech Briefs*, vol. 27, No. 3. pp. 6a-7a. 2003.

* cited by examiner

METHOD AND APPARATUS FOR DETECTING AND QUANTIFYING BACTERIAL SPORES ON A SURFACE

CROSS REFERENCE TO RELATED APPLICATIONS

This application claims the benefit of U.S. Provisional Patent Application Ser. No. 60/519,851 filed on Nov. 13, 2003, which is incorporated herein by reference in its entirety. This application also claims the benefit of U.S. Provisional Patent Application Ser. No. 60/624,068 filed Nov. 1, 2004.

STATEMENT REGARDING FEDERALLY SPONSORED RESEARCH OR DEVELOPMENT

The present invention was made with support from the United States Government under Grant number NAS7-1407 awarded by NASA. The United States Government has certain rights in the invention.

BACKGROUND

1 Field

The present disclosure relates to the field of chemical detection. In particular, a method and apparatus for detecting and quantifying bacterial spores on a surface is disclosed.

2. Description of Related Art

Lanthanide complexes, particularly those of $Tb^{+3}$ and $Eu^{+3}$, exhibit luminescence properties for the detection of aromatic biomolecules. The detection scheme is based on the absorption-energy transfer-emission mechanism, which is triggered by the binding of aromatic ligands to lanthanide complexes under UV excitation. Recent efforts have been focused on the detection of dipicolinic acid DPA (2,6-pyridinedicarboxylic acid), which is a unique constituent of bacterial spores present at high concentrations (up to 1 M). Dipicolinic acid is also a commercially available product having the following characteristics: CAS #: 499-83-2, Synonyms: 2,6 Pyridine Dicarboxylic Acid, Molecular Formula: $C_7H_5NO_4$, Molecular Weight: 167.12, Description: White crystalline powder, Sulphated Ash: 0.3% max, Moisture Content: 0.5% max, Melting Point: 242.0 to 245.0° C., Assay: 99.0% min.

U.S. Pub. App. No. 2003-0138876 for "Method bacterial endospore quantification using lanthanide dipicolinate luminescence" to Adrian Ponce discloses a lanthanide that is combined with a medium to be tested for endospores. Dipicolinic acid released from the endospores binds the lanthanides, which have distinctive emission (i.e., luminescence) spectra, and are detected using photoluminescence. The concentration of spores is determined by preparing a calibration curve that relates emission intensities to spore concentrations for test samples with known spore concentrations. A lanthanide complex is used as the analysis reagent, and is comprised of lanthanide ions bound to multidentate ligands that increase the dipicolinic acid binding constant through a cooperative binding effect with respect to lanthanide chloride. The resulting combined effect of increasing the binding constant and eliminating coordinated water and multiple equilibria increases the sensitivity of the endospore assay by an estimated three to four orders of magnitude over prior art of endospore detection based on lanthanide luminescence.

U.S. Publication application No. 2004-0014154 for "Methods and apparatus for assays of bacterial spores" to Adrian Ponce discloses a sample of unknown bacterial spores which is added to a test strip. The sample of unknown bacterial spores is drawn to a first sample region on the test strip by capillary action. Species specific antibodies are bound to the sample when the unknown bacterial spores match the species specific antibodies, otherwise the sample is left unbound. DPA is released from the bacterial spores in the bound sample. Terbium ions are combined with the DPA to form a Tb-DPA complex. The combined terbium ions and DPA are excited to generate a luminescence characteristic of the combined terbium ions and DPA to detect the bacterial spores. A live/dead assay is performed by a release of the DPA for live spores and a release of DPA for all spores. The detection concentrations are compared to determine the fraction of live spores. Lifetime-gated measurements of bacterial spores to eliminate any fluorescence background from organic chromophores comprise labeling the bacterial spore contents with a long-lifetime lumophore and detecting the luminescence after a waiting period. Unattended monitoring of bacterial spores in the air comprises the steps of collecting bacterial spores carried in the air and repeatedly performing the Tb-DPA detection steps above.

DPA is released from the bacterial spores by microwaving the spores, germinating the spores with L-alanine, sonicating the spores with microspheres or autoclaving the spores. These methods by no means necessarily exhaust the ways in which the DPA can be released from the spores and all other methods of lysing the spores are deemed equivalent.

Exciting the combined terbium ions and DPA generates a luminescence characteristic of the combined terbium ions and DPA. This is achieved by radiating the combined terbium ions and DPA with ultraviolet light.

U.S. Pub. App. No. 2004-0014154 further discloses a method for live/dead assay for bacterial spores comprising the steps of: providing a solution including terbium ions in a sample of live and dead bacterial spores; releasing DPA from viable bacterial spores by germination from a first unit of the sample; combining the terbium ions with DPA in solution released from viable bacterial spores; exciting the combined terbium ions and DPA released from viable bacterial spores to generate a first luminescence characteristic of the combined terbium ions and DPA to detect the viable bacterial spores; releasing DPA from dead bacterial spores in a second unit of the sample by autoclaving, sonication or microwaving; combining the terbium ions with the DPA in solution released from dead bacterial spores; exciting the combined terbium ions and DPA released from dead bacterial spores to generate a second luminescence characteristic of the combined terbium ions and DPA to detect the dead bacterial spores; generating a ratio of the first to second luminescence to yield a fraction of bacterial spores which are alive.

U.S. Pub. App. No. 2004-0014154 further discloses a method for unattended monitoring of bacterial spores in the air comprising the steps of collecting bacterial spores carried in the air; suspending the collected bacterial spores in a solution including terbium ions; releasing DPA from the bacterial spores; combining the terbium ions with DPA in solution; exciting the combined terbium ions and DPA to generate a luminescence characteristic of the combined terbium ions and DPA; detecting the luminescence to determine the presence of the bacterial spores; and generating an alarm signal when the presence of bacterial spores is detected or the concentration thereof reaches a predetermined magnitude.

The step of collecting bacterial spores carried in the air comprises capturing the bacterial spores with an aerosol sampler or impactor. The step of detecting the luminescence to determine the presence of the bacterial spores comprises monitoring the luminescence with a spectrometer or fluorimeter.

Preferably, the step of collecting bacterial spores carried in the air comprises continuously sampling the air and the step of detecting the luminescence to determine the presence of the bacterial spores comprises continuously monitoring the luminescence.

When the step of releasing DPA from the bacterial spores comprises microwaving the bacterial spores to heat the solution, the step of combining the terbium ions with the DPA in solution comprises cooling the heated solution to increase the fraction of bound Tb-DPA complex.

Currently, bioburden levels are determined using the culture-depended methods, with which bacterial spores are quantified in terms of colony forming units (CFU's) that become visible on growth plates after incubation. There are several limitations for culture-depended methods. First, this process requires 3-5 days to complete. Second, a large number of bacterial spores can aggregate on individual particulates giving rise to a single CFU, and thus a large underestimation of the bioburden. Third, colony-counting methods only account for cultivable spore-forming species, which constitute less than 1% in environmental samples.

It is desirable to provide a very sensitive method and apparatus for counting bacterial spores after a short time.

SUMMARY

According to a first aspect, a method for detecting and quantifying bacterial spores on a surface is disclosed, comprising: a) providing a matrix including lanthanide ions on the surface containing the bacterial spores; b) releasing functionalized aromatic molecules from the bacterial spores on the surface; c) forming a complex of the lanthanide ion and the aromatic molecule on the surface; d) exciting the complex of the lanthanide ion and the aromatic molecule to generate a characteristic luminescence of the complex on the surface; and e) detecting and quantifying the bacterial spores exhibiting the luminescence of the complex on the surface.

According to a second aspect, a method for detecting and quantifying bacterial spores on a surface is disclosed, comprising: a) transferring the bacterial spores from the surface containing bacterial spores to a test surface; b) providing a matrix including lanthanide ions on the test surface; c) releasing functionalized aromatic molecules from the bacterial spores on the test surface; d) forming complexes of the lanthanide ions and the aromatic molecules on the test surface; e) exciting the complexes of the lanthanide ions and the aromatic molecules to generate a characteristic luminescence of the complexes on the test surface; and f) detecting and quantifying the bacterial spores exhibiting the luminescence of the complexes on the test surface.

The disclosure also provides an apparatus for detecting and quantifying bacterial spores on a surface including lanthanide ions and aromatic molecules released from the bacterial spores on the surface comprising: an UV light radiation device for exciting a complex of a lanthanide ion and an aromatic molecule to generate a characteristic luminescence of the complex on a surface; a microscope for detecting and quantifying bacterial spores exhibiting the luminescence of the complex on the surface; and an imaging devise for imaging bacterial spores exhibiting the luminescence.

BRIEF DESCRIPTION OF THE DRAWINGS

FIG. 1A is a microscopic image of a spore (about 1 μm in diameter) highlighting a DPA rich spore core.

FIG. 1B is a diagram of a $Tb^{3+}$ ion (shaded ball) which by itself has a low absorption cross section (<10 $M^{-1}cm^{1}$) and consequently has low luminescence intensity. The $Tb^{3+}$ ion can bind the light harvesting DPA (absorption cross section >$10^4$ $M^{-1}$) originating from the spore. DPA binding gives rise to bright Tb luminescence.

FIG. 1C is a diagram of a photophysical scheme for DPA sensitized luminescence of the Tb complex (absorption-energy transfer-emission, AETE).

FIG. 2 depicts a photograph of a backlight illuminated quartz slide with three solidified agar drops. (A) No $Tb^{3+}$ added. (B) $Tb^{3+}$ added but no L-alanine (C) $Tb^{3+}$+L-alanine after germination completion.

FIG. 3 depicts $Eu^{3+}$ microspheres (1-μm) on fluorescent paper imaged with an ImageX-TGi gated CCD camera mounted on a Carl Zeiss fluorescence microscope with 40× objective, excited with a 300-Hz Perkin Elmer flashlamp. Images are obtained (A) without gating, (B) with gating (100-μs delay, 2.7-ms gate), and (C) 100-μm reference graticule to estimate spatial resolution.

FIG. 4 depicts a schematic apparatus for imaging quantifying and counting of bacterial spores.

FIG. 5 depicts two lifetime gated photographs showing bacterial spores on R2A agar before germination (left portion of the figure) and after germination (right portion of the figure).

DETAILED DESCRIPTION

Bacterial spores are generally accepted to be indicator species for validating sterility since they are the most resilient form of life towards sterilization regimens. Sterility testing of surfaces is traditionally performed with RODAC growth plates that require 3-5 days before results are available. The method and apparatus according to the present disclosure will yield results within minutes for obtaining total bacterial spore counts, and an hour for obtaining viable bacterial spore counts on surfaces.

Dipicolinic acid (DPA, 2,6 pyridinedicarboxylic acid) is present in high concentrations (about 1 molar or about 15% of by weight) in the core of bacterial spores 38 as a 1:1 complex with $Ca^{2+}$ as shown in FIG. 1*a*. For all known lifeforms, DPA is unique to bacterial spores and is released into bulk solution upon germination, which is the process of spore-to-vegetative cell transformation. Thus, DPA is an indicator molecule for the presence of bacterial spores. DPA is also a classic inorganic chemistry ligand that binds metal ions with high affinity. DPA binding to terbium ions (or other luminescent lanthanide or transition metal ions) triggers intense green luminescence under UV excitation as shown in FIGS. 1*b* and 1*c*. The green luminescence turn-on signal indicates the presence of bacterial spores. The intensity of the luminescence can be correlated to the number of bacterial spores per milliliter.

The Tb-DPA luminescence assay can be employed to detect bacterial spores on surfaces, including the surfaces of air filters, water membrane filters, and adhesive polymers or agar used to collect bacterial spores from surfaces to be tested. In this disclosure, surfaces to be analyzed with the Tb-DPA assay are called "test surfaces". For example, the Tb-DPA luminescence assay can be combined with an optically transparent, adhesive polymer or agar to collect bacterial spores from surfaces to be tested. Once the bacterial spores are located on the test surface, they can be induced to release their DPA content by germination or physical lysis, for example by autoclaving or microwaving. The highly concentrated DPA from the spores spills into the surrounding area, generating a high concentration region around the spore body. The reagents used for detection and induction of germination, if that is the chosen method for DPA release, can be added into the matrix before or after the spores are sampled. The Tb-DPA luminescence arising from the region around the spore body is then imaged onto a camera. The bacterial spore regions manifest themselves as bright spots which can be counted. Due to the long-lived excited states of luminescent lanthanides, lifetime-gated detection enables any fluorescent background from interferrents to be elimated. Lifetime gating drastically reduces the background and enables much greater contrast between the Tb-DPA luminescence regions and the background.

One example of an adhesive polymer for the Tb-DPA luminescence assay for bacterial spores on surfaces is polydimethyl siloxane (PDMS) doped with $TbCl_3$ and L-alanine. The L-alanine induces germination to release the DPA from the core of the spore to the immediate surroundings. The $TbCl_3$ binds the DPA, which triggers green luminescence (543.5 nm) under UV excitation (250-300 nm) that can be quantified with a photodetector. Specifically, imaging individual germinating spores within a microscope field of view using a lifetime-gated camera will be used as an example.

One example of an adhesive polymer for the Tb-DPA luminescence assay for bacterial spores on surfaces is polydimethyl siloxane (PDMS) doped with $TbCl_3$ and L-alanine. The L-alanine induces germination to release the DPA from the core of the spore to the immediate surroundings. The $TbCl_3$ binds the DPA, which triggers green luminescence (543.5 nm) under UV excitation (250-300 nm) that can be quantified with a photodetector. Specifically, we will use the example of imaging individual germinating spores within a microscope field of view using a lifetime-gated camera.

From the perspective of our sensor design, we treat the bacterial spore essentially as a ~1-μm sphere containing ~$10^9$ molecules of DPA. In our previous experiments, we collected spores from surfaces using the standard cotton swabbing method, resuspended the spores into water, and then released the DPA contents into bulk solution by germination or physical lysing and subsequently performed the Tb-DPA luminescence assay. This approach led to very dilute DPA solutions (e.g., 1 spore per ml of solution yields [DPA]=1 pM), which ultimately limits the sensitivity.

Instead of diluting the DPA into bulk solution, we immobilize the bacterial spores onto an adhesive polymer (e.g., PDMS), and then induce germination or physically lysis in the spore population on the polymer to generate local high DPA concentrations (i.e, the DPA remains in the immediate surroundings of the spore body). To obtain viable counts, germination will be induced by doping L-alanine (or other germination inducing agents) into the polymer matrix; $TbCl_3$, also doped into the polymer, report the presence of bacterial spores by triggering luminescence in the presence of DPA. To obtain total counts, the bacterial spores immobilized on the $TbCl_3$ containing polymer will be physical lysed (e.g., by heat, microwaving, or autoclaving) leads to DPA release and luminescence turn-on.

The present disclosure also includes a method and apparatus to measure the fraction of bacterial spores that remain viable or alive, hence a live/dead assay for bacterial spores. The method combines dipicolinic acid triggered terbium luminescence and dipicolinic acid release from (1) viable bacterial spore through germination, and (2) all viable and nonviable bacterial spores by autoclaving, sonication, or microwaving. The ratio of the results from steps (1) and (2) yield the fraction of bacterial spores that are alive.

The traditional culture based assays require 3 days for colonies to grow and be counted. However, a significant fraction of bacterial spores can undergo stage-1 germination, during which DPA (i.e., the chemical marker that is unique to bacterial spores) is released, in less than 40 minutes. See FIG. 2. A DPA-triggered Tb luminescence with Tb-doped agar was investigated. The samples were prepared by adding ~100 μl of agar doped with 1 mM $TbCl_3$ onto a quartz slide and allowing it to solidify. On top of the agar, we added 10 μl of $10^9$ spores/ml *Bacillus subtilis* spores (i.e., $10^7$ spores), and then added a drop of 10 μl of 1-mM L-alanine to induce germination.

Under UV (blacklight) illumination, the luminescence of the embedded Tb increased dramatically upon germination within 40 minutes of the bacterial spores, while the embedded Tb luminescence in the control sample that had no exposure to L-alanine remained weak. See FIG. 2. An agar control sample without Tb that was covered with bacterial spores also did not yield detectable luminescence. Note that the bright edges of the spots are artifacts of drying due to refraction from accumulated material, which would not appear in a lifetime-gated image.

Figure 2:
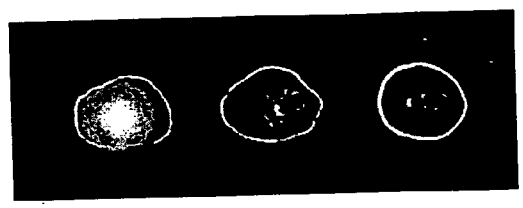

The pictures in FIG. 2 were taken without magnification, and thus the individual spores cannot be enumerated as they germinate. However, in the proposed effort, germinating bacterial spores will be imaged with a lifetime-gated microscope. As the spores germinate, DPA is released from the core to generate local high DPA concentrations, which will show up as bright green luminescent halos surrounding the spore body. These results demonstrate that viable bacterial spores on surfaces by employing the JPL Endospore Viability Assay can be enumerated.

Figure 3:
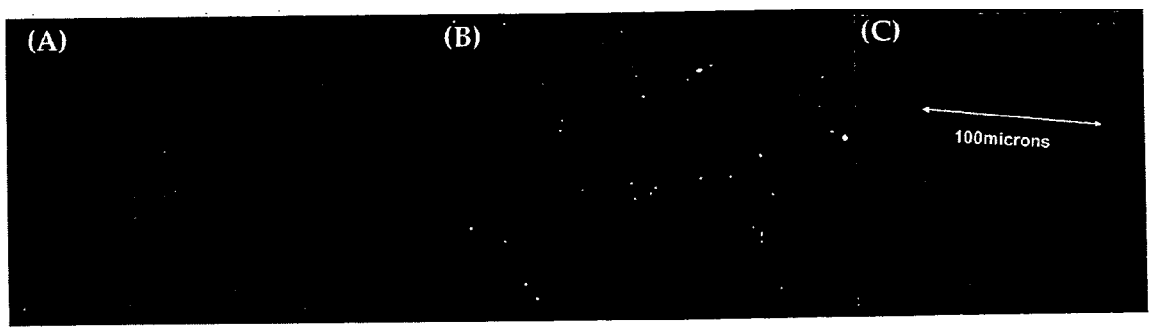

Lifetime-gated images of $Eu^{3+}$ microspheres on highly fluorescent paper were obtained with a lifetime-gated camera (Photonic Research Systems Ltd, United Kingdom). See FIG. 3. $Eu^{3+}$ microspheres were employed because they are commercially available and have analogous photophysical properties. The ImageX system effectively rejected all of the strong background fluorescence when a delay time of 100 μs was used. It is striking that the microspheres exhibiting weak, long-lived luminescence immobilized on a highly fluorescent matrix are imaged with high contrast against a silent background when gating is applied.

Figure 4:
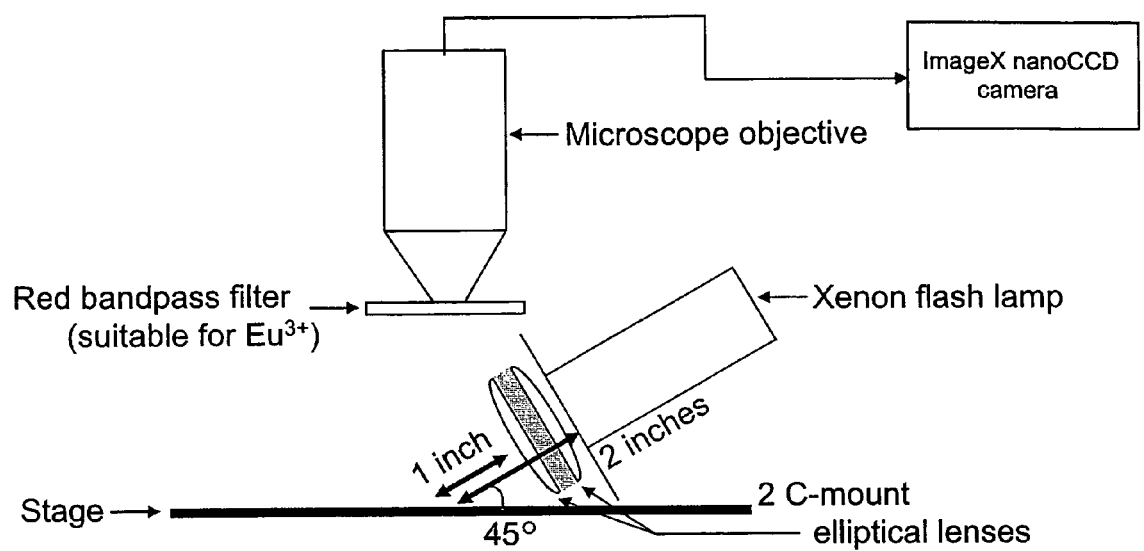
Figure 5:

Another example of the invention is illustrated in FIG. 5, where bacterial spores were added onto the surface of R2A agar doped with 10 mM L-alanine to induce germination and 100 uM $TbCl_3$ to generate bright luminescent spots around the spore body as they germinated and released DPA. A Xe-flash lamp firing at 300 Hz with a 275 nm interference filter provided excitation for the Tb-DPA complex, and the corresponding bright spots from the bacterial spore Tb-DPA luminescent halos where imaged with a lifetime-gated camera set at a delay time of 100 μs and an integration time of 2 ms. The individual bacterial spores become clearly visible as countable spots after they germinated. The images shown in FIG. 5 can be obtained by an apparatus as shown in FIG. 4, which contains a Xenon flash lamp, a microscope objective, a microscope, and a lifetime gated camera mounted on the microscope.

EXAMPLES

Comparative Example 1 Performed According to U.S. Pub. App. No. 2004-0014154

Aerosolized bacterial spores were captured with an aerosol biosampler. The biosampler was filled with 20 ml of 10 μM $TbCl_3$ glycerol solution, which has a 95% transfer efficiency for microbe-containing aerosols. Once bacterial spores were suspended in the biosampler collection vessel, DPA was released by microwave into the bulk solution within 8 minutes. The resulting free DPA then bounded Tb in bulk solution, giving rise to luminescence turn-on under UV excitation. A fiber optic probe immersed in the sample solution transmitted the luminescence to a spectrometer.

Approximately 10,000 bacterial spores per 1 ml solution produced enough DPA to obtain sufficient amount of DPA-Tb complexes to provide enough luminescence turned-on under UV excitation to be detected by a spectrometer.

Comparative Example 2 Performed According to
U.S. Pub. App. No. 2004-0014154

Comparative Example 2 was performed like Comparative Example 1. A fiber optic probe immersed in the sample solution transmitted the luminescence to a fluorimeter.

Approximately 1,000,000 bacterial spores per 1 ml solution produced enough DPA to obtain sufficient amount of DPA-Tb complexes to provide enough luminescence turned-on under UV excitation to be detected by a spectrometer.

Example 1

Bacteria spores were immobilized onto a test sample surface of thin, flexible, clear, adhesive polymer polydimethylsiloxan (PDMS). PDMS was doped with L-alanine to induce germination and generate local high concentration of DPA. $TbCl_3$ was also doped into the PDMS sample. The bacterial spores immobilized on the L-alanine and $TbCl_3$ containing polymer was physically lysed by microwave irradiation, wherein DPA was released and luminescence was turned on. The detection of bacterial spores on the PDMS adhesive polymer was manifested itself as a bright green luminescence that was imaged with a lifetime gated microscope. The green dots within the microscope field of view were counted to determine the concentration of viable spores found on the surfaces that was sampled. Therefore, every bacterial spore releasing luminescence can be individually counted. A concentration of 10,000 bacterial spores per 1 ml as in comparative example 1 or 1,000,000 bacterial spores per 1 ml in comparative example 2 is not required in example 1. As a consequence, the method according to the disclosure can be carried out even with an extremely low concentration of bacterial spores, even a single bacterial spore.

Another embodiment of the present invention is an apparatus for detecting and quantifying bacterial spores on a surface including lanthanide ions and aromatic molecules released from the bacterial spores on the surface. See FIG. 4. The apparatus comprises an UV-light radiation device for exciting a complex of a lanthanide ion and an aromatic molecule to generate a characteristic luminescence of the complex on a surface. The source for the UV-light is preferably a Xenon flash lamp, which is approximately 5 cm away the test surface. Between the Xenon flash lamp and the test surface are two C-amount elliptical lenses. The Xenon flash lamp and the test substrate are positioned in an angel of 45° to each other. The area of irradiation by the Xenon flash lamp is observed by a microscope objective with a red bandpass filter suitable for $Eu^{3+}$ for detecting and quantifying bacterial spores exhibiting the luminescence of the complex on the surface. The image is transferred from the microscope to the imaging devise for imaging bacterial spores exhibiting the luminescence, preferably an imageX nanoCCD camera.

The method and apparatus of the present disclosure provide the imaging of the spherical resolution of the high concentrating region of DPA around each spore body, which has been lysed. The present method makes it possible to detect and quantify extremely low concentrations of bacterial spores in very short time.

Bioburden testing is an assessment of the numbers and types of microorganisms present on a product, and may be used to support sterilization validations. Sterility determination for surfaces are required by the pharmaceutical, health care, and food preparation industries for compliance with bioburden standards as outlined by USP, FDA, PDA, and AAMI.

While several illustrative embodiments have been shown and described in the above description, numerous variations and alternative embodiments will occur to those skilled in the art. Such variations and alternative embodiments are contemplated, and can be made without departing from the scope of the invention as defined in the appended claims.

What I claim is:

1. A method for detecting and quantifying individual bacterial spores on a test surface comprising:
   providing a matrix including one or more lanthanide ions on the test surface containing the bacterial spores;
   releasing functionalized aromatic molecules from the bacterial spores onto the surface;
   forming a complex of the lanthanide ion and the aromatic molecule on the test surface;
   exciting the complex of the lanthanide ion and the aromatic molecule to generate a characteristic luminescence of the complex on the test surface; and
   detecting and quantifying, through lifetime-gated imaging, the individual bacterial spores exhibiting the luminescence of the complex on the test surface.

2. The method according to claim 1, wherein one or more lanthanide ions are provided to the matrix prior to the bacterial spores, after the bacterial spores.

3. The method according to claim 1, wherein the provided lanthanide ions are terbium or europium ions or a mixture thereof.

4. The method according to claim 1, wherein the released aromatic molecules are dipicolinic acid (DPA) and/or derivatives thereof.

5. The method according to claim 1, wherein the aromatic molecules are released from the bacterial spores by microwaving the bacterial spores.

6. The method according to claim 1, wherein the aromatic molecules are released from the bacterial spores by germinating the bacterial spores with L-alanine, inosine and mixtures thereof.

7. The method according to claim 1, wherein the aromatic molecules are released from the bacterial spores by sonicating the bacterial spores with microspheres.

8. The method according to claim 1, wherein the aromatic molecules are released from the bacterial spores by autoclaving.

9. The method according to claim 1, wherein the complex of the lanthanide ion and the aromatic molecule is excited by UV light.

10. The method according to claim 1, wherein the lifetime-gated imaging comprises counting bright spots due to DPA triggered luminescence around the bacterial spores shown in images obtained by a camera, preferably mounted on top of a microscope.

11. The method according to claim 10, wherein the imaging shows the specific resolution of the concentration of dipicolinic acid around the individual bacterial spores, which release dipicolinic acid.

12. A method for detecting and quantifying individual bacterial spores on a surface comprising:

transferring the bacterial spores from the surface containing bacterial spores to a test surface;
providing a matrix including lanthanide ions on the test surface;
releasing functionalized aromatic molecules from the bacterial spores on the test surface;
forming complexes of the lanthanide ions and the aromatic molecules on the test surface;
exciting the complexes of the lanthanide ions and the aromatic molecules to generate a characteristic luminescence of the complexes on the test surface; and
detecting and quantifying through lifetime-gated imaging, the individual bacterial spores exhibiting the luminescence of the complexes on the test surface.

13. The method according to claim 12, wherein the test surface contains at least one polymer.

14. The method according to claim 12, wherein the test surface contains at least one adhesive polymer.

15. The method according to claim 12, wherein the test surface contains at least one adhesive polymer, which is transparent until about 250 nm, thereby providing a transparent test surface.

16. The method according to claim 12, wherein the test surface contains at least one lanthanide ions and L-alanine doped polymer.

17. The method according to claim 12, wherein the test surface contains at least one lanthanide ion and L-alanine doped polydimethylsiloxane polymer.

18. The method according to claim 12, wherein the test surface contains at least one agar.

19. The method according to claim 12, wherein the provided lanthanide ions are terbium or europium ions or a mixture thereof.

20. The method according to claim 12, wherein the released aromatic molecules are dipicolinic acid (DPA).

21. The method according to claim 12, wherein the aromatic molecules are released from the bacterial spores by microwaving the bacterial spores.

22. The method according to claim 12, wherein the aromatic molecules are released from the bacterial spores by germinating the bacterial spores with L-alanine.

23. The method according to claim 12, wherein the aromatic molecule are released from the bacterial spores by sonicating the bacterial spores with microspheres.

24. The method according to claim 12, wherein the complex of the lanthanide ion and the aromatic molecule is excited by UV light.

25. The method according to claim 12, wherein the imaging shows the specific resolution of the concentration of dipicolinic acid around bacterial spores, which release dipicolinic acid.

26. The method according to claim 1, wherein the matrix containing bacterial spores comprises at least one air filter.

27. The method according to claim 12, wherein the matrix containing bacterial spores comprises at least one air filter.

28. The method according to claim 1, wherein the matrix containing bacterial spores comprises at least one water filter.

29. The method according to claim 12, wherein the matrix containing bacterial spores comprises at least one water filter.

30. An apparatus for detecting and quantifying individual bacterial spores on a surface including lanthanide ions and aromatic molecules released from the bacterial spores on the surface comprising:
a test surface having thereon bacterial spores, lanthanide ions and aromatic molecules released from the bacterial spores, wherein the aromatic molecules have been released on the test surface by germination of bacterial spores by the addition of L-alanine, inosine or mixtures thereof or the lysis of bacterial spores by means of one selected from autoclaving, microwaving, heating and sonication;
a UV-light radiation device for exciting a complex of lanthanide ion and aromatic molecule to generate a characteristic luminescence of the complex on the test surface;
a microscope for detecting and quantifying bacterial spores exhibiting the luminescence of the complex on the test surface; and
a lifetime-gated imaging device for imaging bacterial spores exhibiting the luminescence.

31. The method according to claim 1, wherein one or more lanthanide ions are provided as a mixture with the bacterial spores.

* * * * *